United States Patent
Ohtani et al.

[11] Patent Number: 5,891,087
[45] Date of Patent: Apr. 6, 1999

[54] MIXING SYRINGE

[75] Inventors: Seiji Ohtani; Nobuo Tanaka, both of Osaka; Katsuyuki Yokokawa, Settsu; Teruo Matsuda, Tokyo, all of Japan

[73] Assignees: Takeda Chemical Industries, Ltd., Osaka; Arte Corporation, Tokyo, both of Japan

[21] Appl. No.: 818,679

[22] Filed: Mar. 14, 1997

[30] Foreign Application Priority Data

Mar. 15, 1996 [JP] Japan ................................. 8-087688
Nov. 15, 1996 [JP] Japan ................................. 8-321151

[51] Int. Cl.⁶ .................................................. A61M 37/00
[52] U.S. Cl. .......................... 604/89; 604/218; 604/190
[58] Field of Search .................................. 604/190, 191, 604/187, 246, 247, 89, 90, 82, 218, 87, 86; 128/762–766

[56] References Cited

U.S. PATENT DOCUMENTS

| | | | |
|---|---|---|---|
| 4,572,210 | 2/1986 | McKinnon | 604/190 X |
| 4,613,326 | 9/1986 | Szwarc | 604/89 |
| 4,732,162 | 3/1988 | Martell | 604/190 X |
| 4,898,580 | 2/1990 | Crowley | 604/90 |
| 5,395,325 | 3/1995 | Moreno et al. | 604/89 |
| 5,476,449 | 12/1995 | Richmond | 604/87 |

FOREIGN PATENT DOCUMENTS

| | | |
|---|---|---|
| 0568321 | 11/1993 | European Pat. Off. . |
| 9517916 | 7/1995 | WIPO . |

*Primary Examiner*—John D. Yasko
*Attorney, Agent, or Firm*—Wenderoth, Lind & Ponack, L.L.P.

[57] ABSTRACT

Behind a slidable end sealing member 3c, there is provided a liquid-absorbing element M which has a liquid-holding function so as to absorb and hold a liquid L flowing out from the end sealing member 3c when the end sealing member passes over a bypass portion 6. As this liquid-absorbent element M, such as a disk-like element D and a cylindrical element R, are typically impregnated with a water-holding and liquid-absorbing accelerator to enhance a leak preventing effect and with an antimicrobial active agent to enhance hygiene.

28 Claims, 13 Drawing Sheets

MIXING SYRINGE

BACKGROUND OF THE INVENTION

1. Field of the Invention

The present invention relates to a syringe with a liquid leak preventing mechanism, and specifically to a mechanism for preventing liquid leaking from syringe.

2. Description of Related Art

In a two-ingredient type pre-filled syringe charged with a predetermined medicine and a liquid such as its dissolution liquid, its dispersing liquid or other medicinal liquids in separated states, of the disposable type syringes previously filled with a medicine, so-called pre-filled syringes, conventionally as exemplified in FIG. 10, there has been known in Japanese Patent Publication No. 49-14465 a syringe having a construction such that an end sealing member 32 is inserted through a rear end opening into a cylindrical receptacle or barrel 31 provided at its leading end portion with a mounting portion for a needle. The barrel 31 has an intermediate sealing member 33 arranged therein so as to be slidable in a longitudinal or axial direction and to have a first chamber 34 on the leading end side and a second chamber 35 on the rear end side, divided therein to receive a medicine P and a dissolution liquid L within the respective chambers, and with its leading end portion closed by a cap 37.

This one type has such a construction that the first chamber 34, on the leading end side ahead of the intermediate slidable sealing member 33, has a bypass portion, usually an outwardly protruded bypass channel 36, arranged in the side wall of the barrel 31. At the time of use, the intermediate sealing member 33 is advanced together with the liquid L within the second chamber 35 by pushing the end sealing member 32 by means of a rod as shown in FIG. 11, and the liquid L within the second chamber 35 is made to flow into the first chamber 34 through the bypass channel 36 when the intermediate sealing member 33 reaches the channel 36. As shown in FIG. 12, subsequently thereto, the intermediate sealing member 33 is pushed by the leading end of the end sealing member 32 to perform the dissolution, the dispersion or the mixing within the first chamber 34, and then the liquid is pushed out of the leading end.

Since the end sealing member passes the bypass portion, the liquid remaining in the bypass portion leaks behind the end sealing member. Therefore, a mechanism for preventing a liquid leak outside of the syringe, by arranging a partition plate behind the end sealing member was proposed in Japanese Patent Publication (unexamined) No. 62-14863.

In this method, however, a low-viscosity medicinal liquid, a small surface-tension liquid and the like happen to pass through a gap between the partition plate provided in the plunger rod and the barrel inner wall, and it is apprehended that the medicinal liquid remaining in the partition plate flows out when the plunger rod is removed from the syringe for fractional scrapping.

Therefore, it is an object of the invention to provide a syringe with a liquid leak preventing mechanism which is capable of preventing a medicinal liquid from passing out through a gap between a receptacle or barrel inner wall and a partition plate and also from flowing out when a plunger rod is dismounted from the syringe for fractional scrapping.

SUMMARY OF THE INVENTION

According to a first aspect of the present invention, there is provided a syringe comprising:

a tubular barrel having distal and proximal end portions opposite to each other and also having an interior hollow defined therebetween, the distal end portion being sealed and engageable with a needle for injection of medical substances to be mixed in the hollow and the proximal end portion being sealed by a slidable end sealing member connectable with a plunger rod for making the end sealing member slidable in an axial direction in the barrel;

at least one intermediate sealing member inserted into the barrel, the intermediate sealing member dividing the hollow of the barrel in a sealed manner into a first chamber for receiving a first medical substance and a second chamber for receiving a second medical substance, the intermediate sealing member being slidable in the barrel in response to sliding of the end sealing member in the barrel;

at least one bypass portion formed axially along the barrel between the intermediate sealing member and the distal end portion, the bypass portion permitting the second medical m substance to bypass the intermediate sealing member and be introduced into the first medical substance to be mixed therewith;

wherein the intermediate sealing member has an axial length or thickness shorter than that of the bypass portion;

at least one liquid-absorbent element capable of absorbing the liquid and holding it therein, the liquid-absorbent element being positioned behind one of end face of the end sealing member opposite to the second chamber in the barrel.

In the present invention, the meaning of "positioned behind one end face of the end sealing member opposite to the second chamber in the barrel" includes any case where the liquid-absorbent element is positioned behind the end sealing member with respect to a longitudinal direction of the barrel. For example, in one case, the liquid-absorbent element may be positioned at no or some interval from the end face of the end sealing member with respect to the longitudinal direction of the barrel. In another case, the liquid-absorbent element may be positioned as an end stopper for closing an end opening of the barrel.

Therefore, in the case of a two-chamber syringe including at least one intermediate slidable sealing member inserted into a cylindrical barrel having a leading end portion to which a needle is mounted and a rear end opening into which a plunger rod is inserted, the barrel is divided into a forward first chamber and a rearward second chamber by the intermediate sealing member, the first chamber receiving a certain medicine and the second chamber receiving a liquid to be mixed with the medicine. The rear end side of the rearward second chamber which has received the liquid can be closed by inserting therein an end slidable sealing member adapted to be pushed by a leading end of the plunger rod. The intermediate slidable sealing member is displaced forwards to a region of the bypass portion by means of the plunger rod, so that the liquid within the second chamber can be made to flow into the first chamber through the bypass portion and is mixed with the medicine within the first chamber. The liquid-absorbent mechanism or element is arranged behind the end slidable sealing member with no or some intervals and is capable of absorbing and holding the liquid flowing out behind the end sealing member.

According to the present invention, when the end slidable sealing member passes absolutely over the bypass portion, the liquid flowing out behind the end slidable sealing member is absorbed and held by the liquid-absorbent mechanism, so that it is possible to prevent the liquid leakage and dispersion out of the syringe barrel even when the plunger rod after use is removed at the time of fractional scrapping.

Generally, the syringe barrel is transparent so that the residual liquid can be seen from the outside, and it is apprehended that the leak occurs because the syringe barrel is merely shielded. According to the present invention, the liquid itself is securely held in the absorbed and held condition, so that it becomes possible to resolve such a problem.

Especially in the case where the liquid-absorbent material is impregnated with a water-holding and liquid-absorbing agent, it is possible to perfectly attain a liquid-absorbent and holding effect even though a clearance exists between the liquid-absorbent element and the inner surface of the syringe.

Further, since microorganisms tend to increase in the liquid-absorbent material owing to its material property, the material can contain an antimicrobial active agent, either together with the water-holding and liquid-absorbing agent or separately. Therefore, it is possible to prevent an increase of the microorganisms which tend to grow in the liquid-absorbent material and thereby to enhance safety at the time of fractional scrapping.

BRIEF DESCRIPTION OF THE DRAWINGS

The above and other objects and features of the present invention will become more apparent from the following description of a preferred embodiment thereof with reference to the accompanying drawings, throughout which like parts are designated by like reference numerals, and wherein:

FIGS. 2A and 2B are explanatory views of an assembling procedure of a syringe main body including the charging of medicine and the like;

DETAILED DESCRIPTION OF THE PREFERRED EMBODIMENTS

A liquid absorbing mechanism or element M may be mounted in the barrel by three ways as follows.

Figure 13:
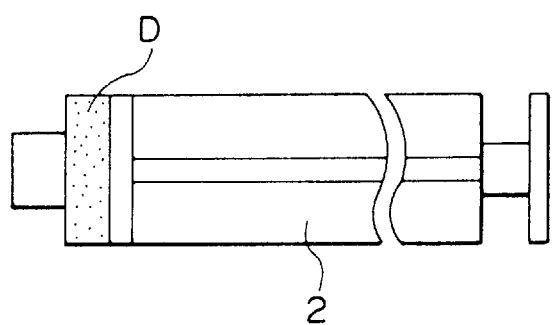
FIG. 13 is a schematic view showing an arrangement of a first embodiment of a liquid leak preventing mechanism for use in the present invention.
Figure 14A:
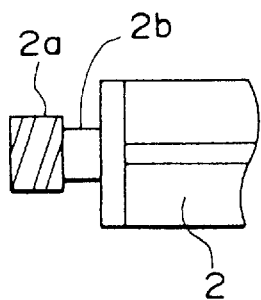
FIGS. 14A and 14B are side views showing a first attaching mechanism of the first embodiment.
Figure 14B:
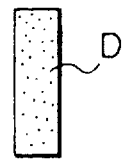
Figure 15A:
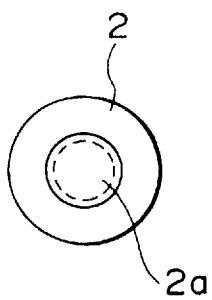
FIGS. 15A and 15B are front views showing the first attaching mechanism of the first embodiment.
Figure 15B:
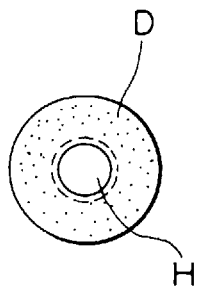
Figure 16A:
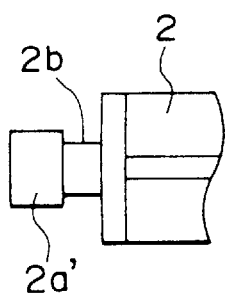
FIGS. 16A and 16B are side views showing a second attaching mechanism of the first embodiment.
Figure 16B:
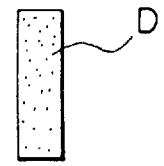
Figure 17A:
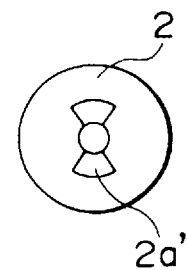
FIGS. 17A and 17B are front views showing the second attaching mechanism of the first embodiment.
Figure 17B:
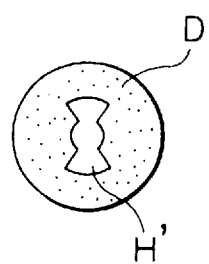

1) The liquid absorbing element may be mounted integrally or detachably on the backside of an end slidable sealing member which is mounted integrally or detachably on one end portion of the plunger rod inserted within the barrel. Accordingly, as shown in FIG. 13, it may be constructed by attaching to the leading end of the plunger rod 2 a slidable disk-shaped liquid-absorbent material D selected from the group consisting of a filter paper, a nylon felt, a cotton non-woven fabric, fibers such as yarn or fabric, or resin such as a water absorbing polymer. As shown in FIGS. 14 and 15, threads are formed at a leading protruded portion 2a of the rod 2 while a threaded hole H is formed in the disk-shaped liquid-absorbent material D at its center so as to be threadably engaged and fitted into a groove 2b. Further, as shown in FIGS. 16 and 17, a twist lock is formed at a leading end portion 2a' of the rod 2 while a twist hole H' is formed in the disk-shaped liquid-absorbent material D at its center so as to be engaged by the twisting and fitted into the groove 2b. Furthermore, a plurality of disk-shaped liquid-absorbent materials D may be prepared and arranged in a stacked manner or in a spaced apart manner.

Figure 25:
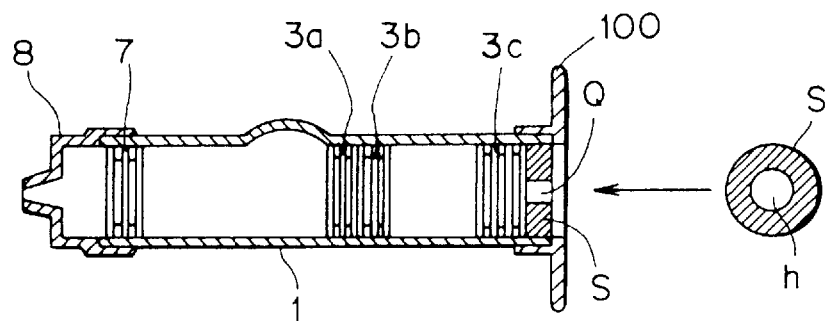
FIG. 25 is a sectional side view showing a first liquid-absorbent end stopper for use in the present invention.
Figure 26:
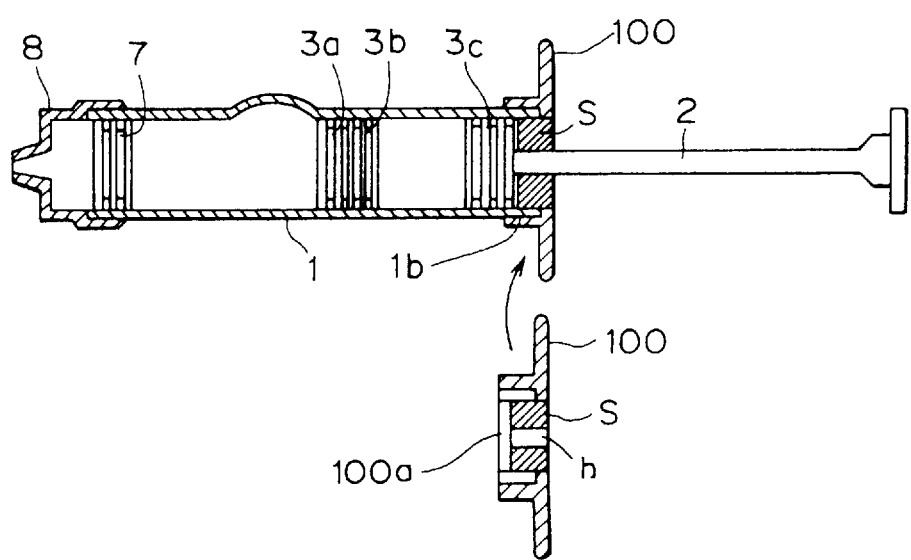
FIG. 26 is a sectional side view showing a second liquid-absorbent end stopper for use in the present invention.

2) On the other hand, the liquid-absorbent element M may be positioned at one end of the barrel as an end stopper for closing an end opening in a separate manner from the end slidable sealing member. Accordingly, as shown in FIG. 25, a disk-shaped end stopper S similar to the liquid-absorbent material D has a through hole (h) for receiving the rod 2 at the center thereof and is arranged in a non-slidable manner just behind the backside of end sealing member 3c. Further, as shown in FIG. 26, the disk-shaped end stopper S has also a through hole (h) for receiving the rod 2 at the center and may be fitted in a receiving space within a fitting cap portion 100a of a finger D grip 100 which is mounted on an end 1b of the barrel 1.

3) Further, the liquid-absorbent element M may be the disk-shaped material D mounted on the backside of the end sealing member in a slidable manner and additionally include the end stopper S mounted at the end of the barrel in a non-slidable manner.

Figure 18:
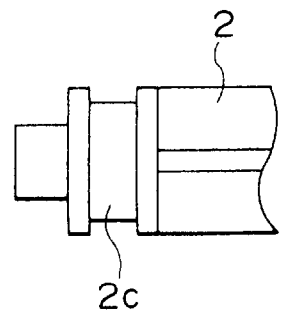
FIG. 18 is a side view showing an attaching mechanism of the second embodiment.
Figure 19:
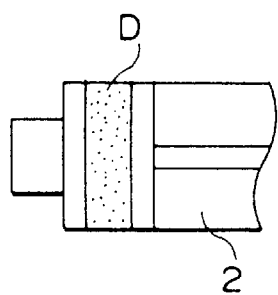
FIG. 19 is a schematic view showing an arrangement of a second embodiment of the liquid leak preventing mechanism for use in the present invention.

The liquid-absorbent element M can be provided by winding the filter paper or the fibers in the form of yarn, fabric, or non-woven fabric around a winding groove 2c formed at the leading end of the plunger rod 2 as shown in FIG. 18 (refer also to FIG. 19). Though FIG. 19 shows one which is mounted only to the leading end by winding, it may be wound along the longitudinal direction of the plunger rod. By the way, since an external configuration of the liquid-absorbent material defines a clearance relative to an inner wall of the syringe, in consideration of a surface tension and viscosity of the liquid, the clearance may be made small so as to become 0.2–1.0 mm in the case of a liquid having a small surface tension, like an alcohol, and may be made large so as to become 0.2–1.5 mm in the case of a liquid having a comparatively large surface tension, like water.

Figure 20:
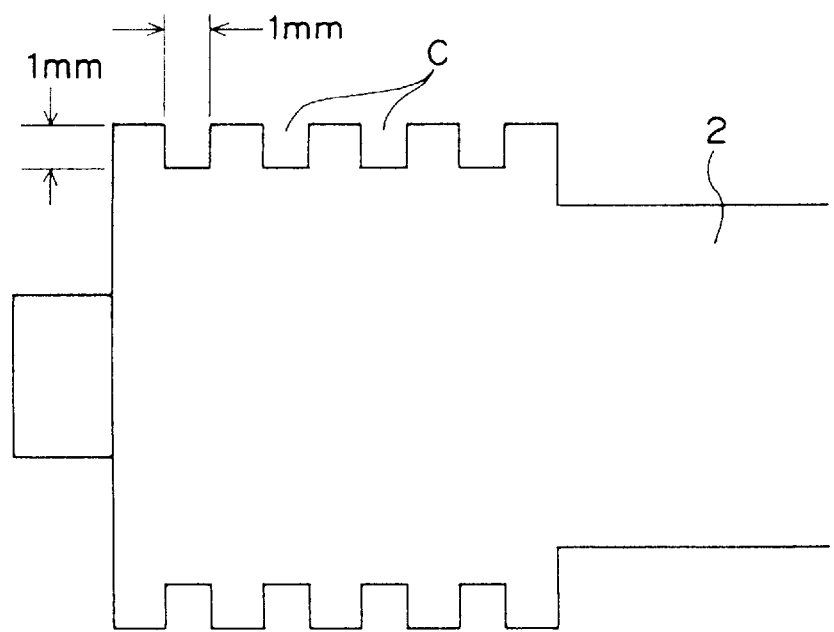
FIG. 20 is a schematic view showing an arrangement of a third embodiment of the liquid leak preventing mechanism for use in the present invention.
Figure 21:
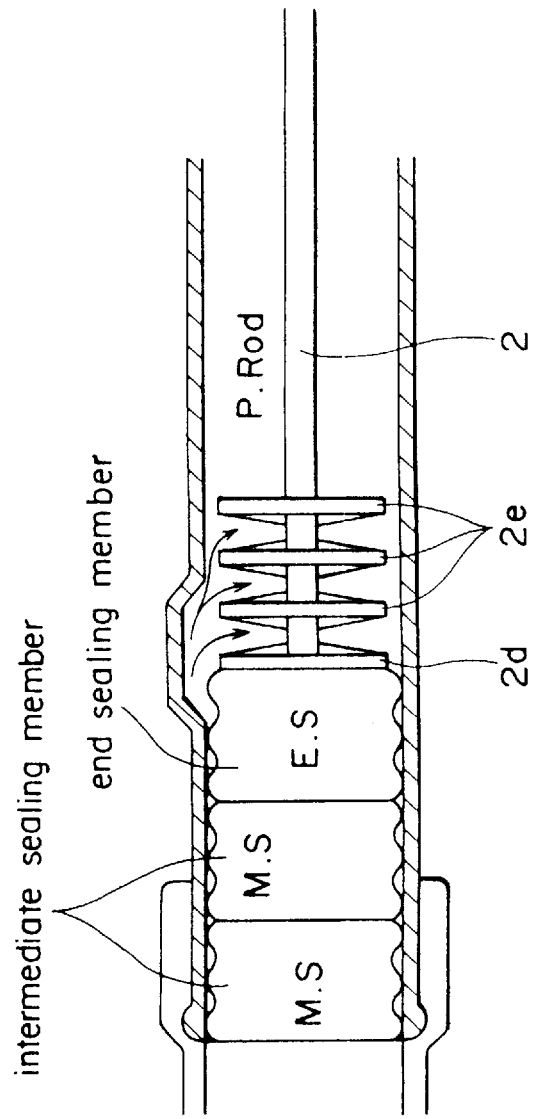
FIG. 21 is a schematic view showing a variant example of the third embodiment of the liquid leak preventing mechanism for use in the present invention.

Though the above-mentioned liquid-absorbent element M is embodied by the material to have liquid absorbing capability, it may be constructed by utilizing the capillary phenomenon provided by annular or spiral liquid absorbing grooves C formed at the leading end of the plunger rod 2 as shown in FIG. 20. Further, as shown in FIG. 21, the grooves may be provided by arranging a plurality of disks 2e side by side in a stacked state in addition to and behind a disk 2d at the leading end of the plunger rod 2. Also in this case, it is preferable to define a groove width and depth in consideration of the viscosity and the surface tension of the liquid.

Figure 22:
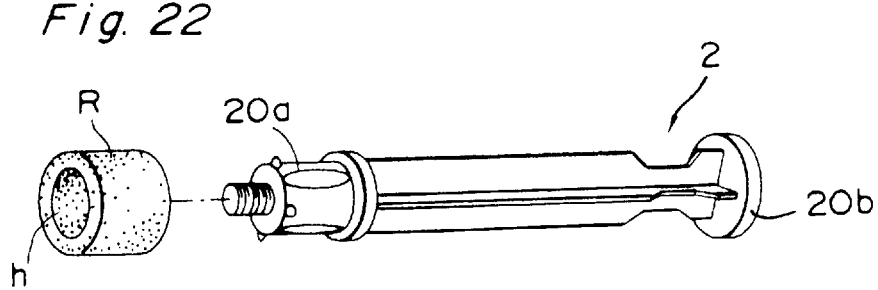
FIG. 22 is a perspective view showing a fourth embodiment of the liquid leak preventing mechanism for use in the present invention.

Further, as shown in FIG. 22, the above-mentioned liquid-absorbent element M may comprise a cylindrical barrel formed of a slidable cylindrical liquid-absorbent material R which is detachably mounted to the leading end portion of the plunger rod 2. In detail, a threaded portion to which the end sealing member 3c is mounted by being fixedly secured by means of threads is projected from a leading end 20a of the plunger rod 2, and four shallow grooves as stoppers for preventing rotation of the liquid-absorbent material R are formed surrounding the leading end 20a and four lugs are formed therebetween to prevent removal of the liquid-absorbent material R. A radius of this leading end portion 20a is a little larger than a radius of a hole of the liquid-absorbent material R.

Figure 23:
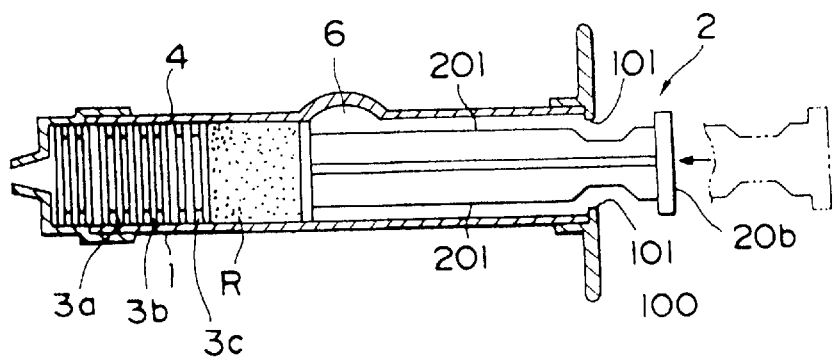
FIG. 23 is a sectional side view showing a first mode pushing-in condition of the fourth embodiment of the liquid leak preventing mechanism for use in the present invention.
Figure 24:
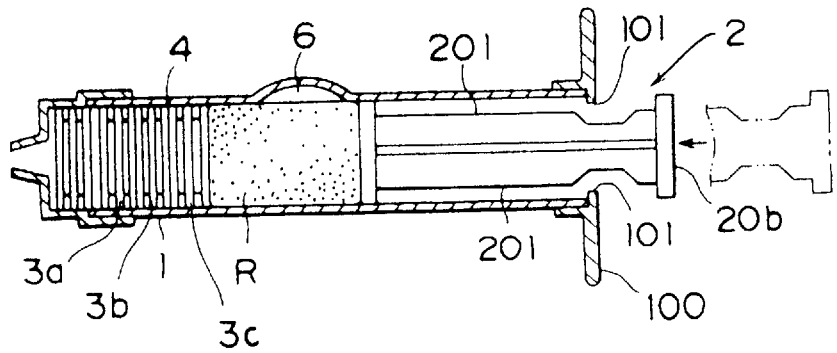
FIG. 24 is a sectional side view showing a second mode pushing-in condition of the fourth embodiment of the liquid leak preventing mechanism for use in the present invention.

Incidentally, 20b designates a pushing portion of the rod 2. In this case, as shown in FIG. 23, since an entire length of the cylindrical liquid-absorbent material R is longer than that of the disk-shaped liquid-absorbent material D as shown in FIG. 15 in a longitudinal direction of the barrel or the advancing direction of the plunger rod 2, even though a dropping timing of the residual liquid gets delayed when passing over the bypass portion of the syringe, satisfactory liquid absorption and holding becomes possible. Usually, it is preferable to set its total length to at least 10 mm. When this end slidable sealing member is fully pushed in, usually the cylindrical liquid-absorbent material R is pushed forward beyond the bypass portion. Thereupon, however, especially as shown in FIG. 24, when its rear end is adapted to block the bypass portion to make the liquid remain there, the residual liquid can be greatly effectively prevented from leaking.

The liquid-absorbent material is preferably at least one kind of material selected from the group consisting of polyvinylformal, polyester fiber, pulp, polyester fiber containing pulp or acetate fiber, cellulose sponge, polyvinylformal sponge (PVA sponge available from KANEBOU Co. Ltd. in Japan) and liquid absorbent resin. The liquid-absorbent material is preferably impregnated with a water-holding and liquid-absorbing accelerator for accelerating its liquid-absorbing effect. This water-holding and liquid-absorbing accelerator is selected from the group consisting of glycerine, propylene glycol, polyethylene glycol, D-sorbitol, polyoxyethylene cetyl ether, and benzyl alcohol, and the impregnation is performed by dipping the liquid-absorbent material into the medium such as a water containing 1–30 weight percent thereof. Thereupon, an interfacial active agent such as polysolvate 80 may be added thereto for use.

The liquid-absorbent material may contain an antimicrobial active agent. The antimicrobial active agent is at least one kind of material selected from the group consisting of benzalkonium chloride, benzethonium chloride, dodecyldiaminoethylglycine, dodecyldimethylbenzylammonium chloride, polyhexamethylenebiguanide, cetylpyridium chloride and alkyldiaminoethylglycine hydrochloride, and its amount can be adjusted in accordance with the use condition.

In case of using a colored liquid mixed with the medicine, or a colored mixture, the liquid-absorbent material may be colored to make invisible, through a transparent barrel, colored traces caused by the liquid or the mixture absorbed therein. Examples of the coloring agent are Powdered Catechutannic Acid, Indigocarmine, Turmeric Extract, Methylrosanilinium Chloride, Yellow Oxide of Iron, Yellow Ferric Oxide, Opalux AS-6178 (Trademark of NIHON Calacon Co. Ltd.), Carbon Black, Color Paste 1, Color Paste 2, Color Paste 3 (Trademark of NIHON Calacon Co.

Ltd.), Caramel, Carmine, β-Carotene, Carotene Solution, Gold Leaf, Black Oxide of Iron, Kekketsu, Zinc Oxide, Titanium Oxide, Real Ferric Oxide, Dis Azo Yellow, Food Yellow No. 4, Food Yellow No. 5, Food Blue No, 1, Food Yellow No. 4 Aluminum Lake, Food Red No. 102, Food Red No. 2, Food Red No. 3, Zein, Taiyo Caramel, Sodium Copper Chlorophyllin, Copper Chlorophyll, Phenol Red, Powdered Tea, Octyldodecyl Myristate, Methylene Blue, Medicinal Carbon, Riboflavin Butyrate, Riboflavin, Powdered Green Tea, Ammonium Manganese Phosphate, Riboflavin Sodium Phosphate, and Rose Oil.

In case the liquid or mixture has a pharmacological L5 activity, the liquid-absorbent material may contain a deactivating agent, which may be selected from the group consisting of Ethanol, Methanol, Hydrogen Peroxide, Sodium Hypochlorite, Sodium Hydroxide, Potassium Hydroxide, Magnesium Hydroxide, Sodium Hydrogencarbonate, Sodium Carbonate, Boric 0 Acid, Sulfuric Acid, Phosphoric Acid, Tri-sodium Phosphate, Di-sodium Phosphate, Tri-potassium Phosphate, Di-potassium Phophate, Hydrochloric Acid, Lactic Acid, Aqueous Ammonia, Hydrargyrum and so on.

According to the present invention, a larger effect for preventing leakage can be obtained in an embodiment having substantially no clearance between the outer circumference of the liquid-absorbent element and the inner wall of the syringe. However, the clearance can make it possible to improve the slidability of the liquid-absorbent material and to simplify fragmental scrapping. In the case where the syringe is provided at its rear end with a finger grip, it becomes necessary to provide the clearance depending on a configuration of the grip. In the case where the liquid-absorbent material has the clearance between its outer circumference and the inner wall of the syringe, the liquid absorbing rate decreases a little. But, the liquid absorbing rate can be improved to 100% by making the material contain a water-holding and liquid absorbing accelerator.

The two-chamber type syringe according to the present invention can be applied to the following mode. The liquid leak preventing element is designated by M in the respective drawings. As its function and construction are the same as the above-mentioned ones, explanations thereof will be omitted.

Figure 1:
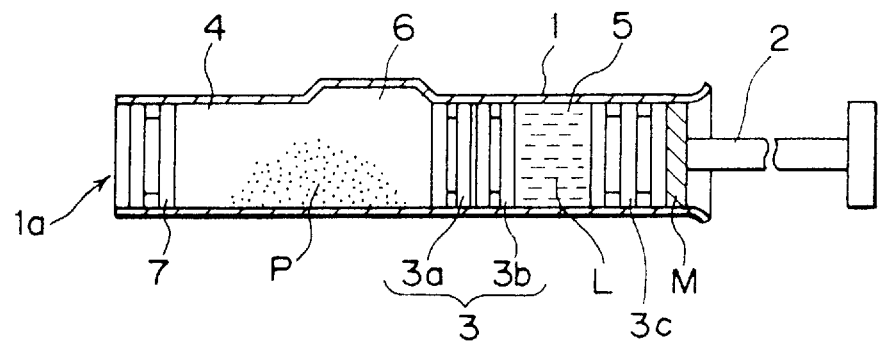
FIG. 1 is a sectional view showing a basic construction of an embodiment of the present invention.

FIG. 1 is a sectional view showing a basic construction of a practical mode of the present invention.

The cylindrical barrel 1 is uniformly cylindrical as a whole except for a bypass channel 6 defining the bypass portion to be described later and has its opposed ends fully opened.

The end slidable sealing member 3C mounted to the rod 2 is inserted into this cylindrical barrel 1 from its rear end side, and an intermediate slidable sealing member 3 is inserted therein so as to divide the interior of the barrel 1 into a first chamber 4 and a second chamber 5. This slidable sealing member 3 is divided into a forward slidable sealing member 3a and a rearward slidable sealing member 3b. These forward slidable sealing member 3a and rearward slidable sealing member 3b may be in contact with each other or have a predetermined space therebetween as illustrated. In order to provide such a space therebetween, a suitable lug may be formed in at least one of the opposed surfaces of the forward slidable sealing member 3a and the rearward slidable sealing member 3b.

A sealing member 7 is mounted to the leading end opening portion 1a of the cylindrical barrel 1. Incidentally, for example a cap with a needle may be mounted to the leading end portion of this cylindrical barrel 1 when we need injection as described later, or the needle may be mounted thereto by such a known means as to attach a double-pointed needle to a holder member and make its Tear end pierce through the sealing member 7.

The first chamber 4 is charged with powder medicine P and the second chamber 5 is charged with a dissolution liquid, a dispersion liquid or various kinds of medicinal liquids L, respectively. The bypass channel 6 is formed in a side wall of the first chamber 4 of the cylindrical barrel 1 so as to have a predetermined width and to swell or protrude outward. A length of this bypass channel 6 in the axial direction of the cylindrical barrel 1 is set longer by a predetermined degree than a total length of both the forward slidable sealing member 3a and the rearward slidable sealing member 3b. Further, a total length of the slidable sealing members 3a, 3b and the end portion sealing member 3c in the axial direction is set longer by a predetermined degree than an axial length of the bypass channel 6. This length adjustment can be readily made by regulating a length of the end slidable sealing member.

In the practical mode of the present invention having the above-mentioned construction, similarly to the conventional one, both the forward slidable sealing member 3a and the rearward slidable sealing member 3b are advanced via a body of the liquid L within the second chamber 5 by pushing the end slidable sealing member 3c mounted on the rod 2 (referred to as a plunger member hereinafter) toward its leading end side. These reach the formation position of the bypass channel 6 so that the first chamber 4 and the second chamber 5 are put in communication with each other. Thereupon, the liquid L within the second chamber 5 flows into the first chamber 4. After this flowing-in is completed and the leading end of the plunger member 3c is moved to the rear end of the rearward slidable sealing member 3b, this member 3b is directly pushed to advance the forward and rearward slidable sealing members 3a, 3b and to stop the pushing at a position where at least a fore half portion of the forward slidable sealing member 3a reaches ahead of the leading end portion of the bypass channel 6 and at least a rear half portion of the sealing member 3c of the plunger member does not reach the bypass channel 6 to hold the slidable condition relative to the inner wall of the cylindrical barrel 1. Then, after the mixing and so on are completed by shaking the cylindrical barrel 1, the injection liquid prepared by the dissolution, the dispersion or the mixing is injected through the needle mounted to the leading end of the barrel 1. Thereupon, the liquid leak preventing element M absorbs and holds the residual liquid within the bypass channel.

Figure 2A:
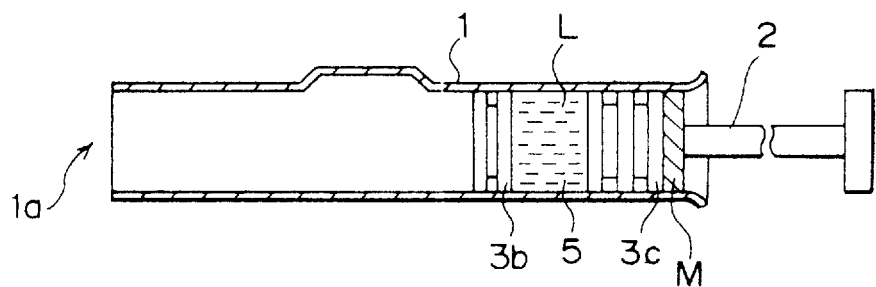
Figure 2B:
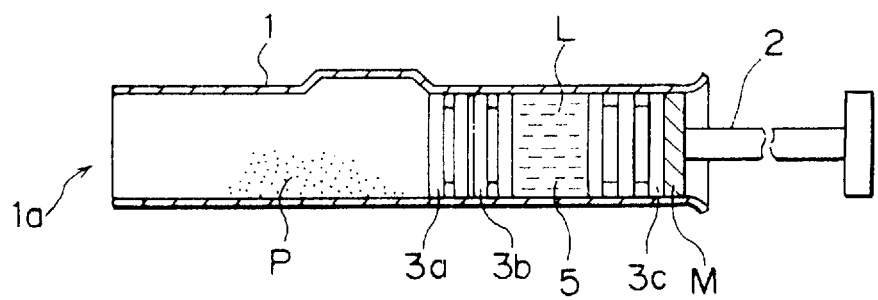

Next, the procedures of assembling the syringe main body including charging of the powder medicine, the dissolution liquid and so on in the above-mentioned practical mode of the present invention are shown in FIGS. 2A and 2B.

First, as shown in FIG. 2A, the dissolution liquid, the dispersion liquid or the medicinal liquid L is charged into the second chamber 5 and the end portion sealing member 3c is inserted therein on the condition that the rearward slidable sealing member 3b is inserted into the cylindrical barrel 1. After sterilization for the dissolution liquid, the dispersion liquid or the medical liquid L, made by steam heating in this condition, the inner surface of the first chamber 4 is dried. At this steam heating sterilizing treatment, the dissolution liquid, the dispersion liquid or the medicinal liquid L within the second chamber 5 containing an activation substance is treated at such a temperature as not to destroy the substance, for example at most 50°–60° C.

After that, as shown in FIG. 2B, the forward slidable sealing member 3a is inserted into the cylindrical barrel 1 through its leading end opening portion 1a in the previously sufficiently dried-up condition to be brought into intimate contact with the rearward slidable sealing member 3b or at a position near thereto spaced apart a very short distance. After the powder medicine P is charged into the first chamber 4 through its leading end opening portion 1a in that condition, the two-ingredient pre-filled syringe shown in FIG. 1 can be obtained by mounting the stationary sealing member 7 to the leading end opening portion 1a. In this case, there may be employed either one of the rods 2, mounted originally or mounted later.

In the above-mentioned assembling procedures, moisture tends to attach to or penetrate the rearward slidable sealing member 3b at the time of steam heating sterilization of the dissolution liquid, the dispersion liquid or the medicinal liquid L within the second chamber 5. It is possible to prevent transfer of the moisture to a side of the powder medicine P by inserting the dried forward slidable sealing member 3a and then charging the powder medicine P into the first chamber 4 after the steps of steam heating sterilization, drying and cooling.

With a space between the forward and the rearward slidable sealing members 3a, 3b, the time required for moisture to enter the forward slidable sealing member 3a from a side of the second chamber 5 through the rearward slidable sealing member 3b in a stored state after assembly becomes longer, and it becomes possible to elongate the period of time required for the moisture to reach the medicine in the first chamber 4.

Although it was already described that the above two-ingredient prefilled syringe according to the present invention is used with the needle mounted to the leading end of the cylindrical barrel 1, there will be explained hereinafter more concrete structural examples of the needle mounting element, the sealing member 7 at the leading end opening portion 1a of the cylindrical barrel 1, the slidable sealing member 3a and so on.

EXAMPLES

Figure 3:
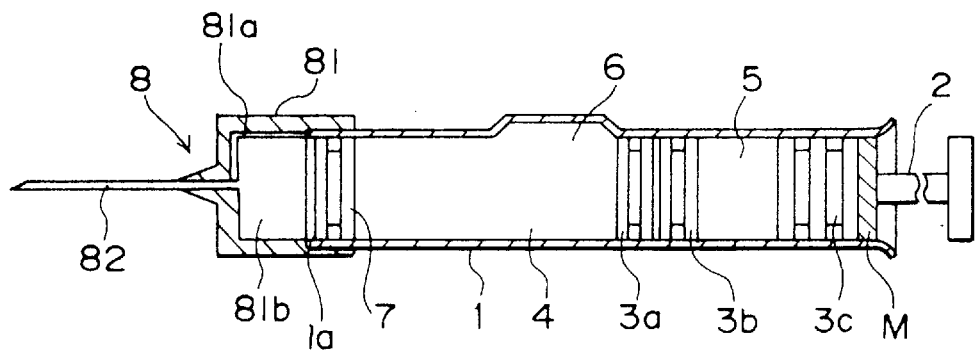
FIG. 3 is a sectional view showing a construction of a concrete embodiment of the present invention in a case where a movable type sealing member is employed at a leading end opening portion of a cylindrical barrel.

FIG. 3 is a sectional view showing an example in which a slidable type sealing member 7 to be inserted into the leading end opening portion of the cylindrical barrel 1 is used.

This example shows a barrel 1 wherein a cap 8 is mounted with the needle onto a distal end thereof. The cap 8 has a needle 82 mounted to a tip end of a cup-shaped cap main body 81 and has such a construction that a groove 81a communicating with the needle 82 is formed in the inner circumference of the main body 81. Further, the main body 81 has a void space 81b which projects toward the distal end side from the end opening portion 1a of the cylindrical barrel 1 by a predetermined distance and into which the sealing member 7 can be inserted.

Figure 4:
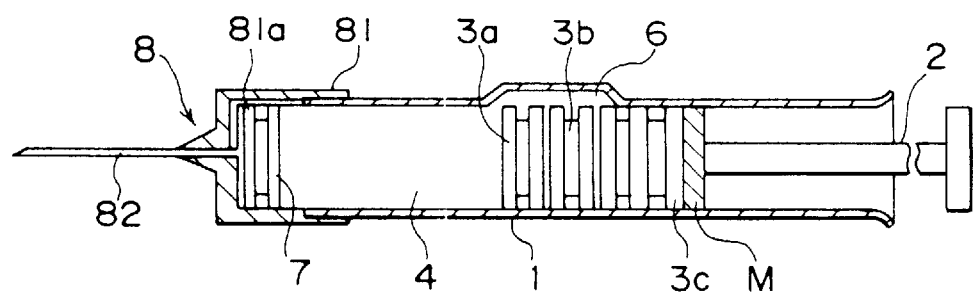
FIG. 4 is an explanatory view of a function during the use of the embodiment of FIG. 3.

Under such a condition, when the dissolution liquid, the dispersion liquid or other kinds of medicinal liquids within the second chamber 5 flow into the first chamber 4 through the bypass channel 6 by pushing the rod 2 as shown in FIG. 4, the sealing member 7 is moved into the void space of the main body 81 of the cap 8 with the needle. When further pushing the rod 2 under this condition, the injection liquid within the first chamber 4 enters the needle 82 through the groove 81a formed in the main body 81 of the cap 8 and is then injected. The cap 8 with the needle may be prepared at the time of injection or may already be mounted before the injection.

Instead of the above-mentioned construction, the sealing member 7 may be constructed so as to be spaced apart a short distance from the leading end of the cylindrical barrel 1 when the sealing member 7 is arranged within the barrel 1 and stay at the leading end portion of the cylindrical barrel 1 when the flow of the liquid within the second chamber 5 into the first chamber 4 by the plunger 2 is completed. Since the fore and rear ends of the first chamber 4 are completely closed, even when the barrel 1 is shaken when dissolving or dispersing, the liquid does not leak from anywhere.

Figure 5:
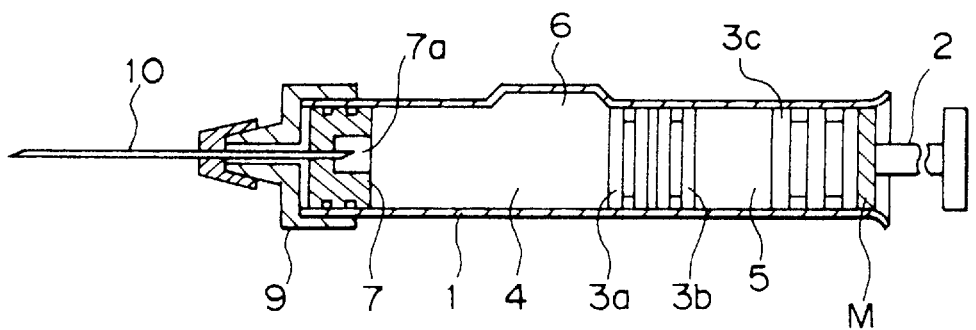
FIG. 5 is a sectional view showing another embodiment of the present invention in a case where an immovable type sealing member is employed at the leading end opening portion of the cylindrical barrel and a double-pointed needle is used as a needle.

FIG. 5 is a sectional view showing an example in which, as the sealing member 7, a stationary type is used. In this type, a double-pointed needle 10 has at its rear end portion put through the sealing member 7 so as to project into the first chamber 4 by mounting a cap 9 serving also as a needle holding member to the leading end portion of the cylindrical barrel 1 and inserting the double-pointed needle 10 through this cap 9 to a predetermined position.

In this construction, since the needle is soon communicated with the first chamber 4 by mounting the double-pointed needle 10, it becomes possible to inject the injection liquid within the first chamber 4 directly through the interior of the double-pointed needle 10, similarly to the above-mentioned case.

In this way of employing the double-pointed needle 10, since the rear end portion of the needle 10 passes through the sealing member 7 to enter the first chamber 4, as shown in FIG. 5, it becomes possible to decrease the quantity (a loss quantity) of the residual injection within the cylindrical barrel 1 during injection by previously forming, in the end face of the sealing member 7 on the side of the first chamber 4, a concave portion 7a capable of receiving a projecting length of the needle.

In the two-ingredient pre-filled syringe, the liquid L within the second chamber 5 nearly completely flows into the first chamber 4 by pushing the plunger rod 2 prior to an actual injection, so that two-ingredients are dissolved, dispersed or mixed uniformly within the first chamber 4. The liquid doesn't flow out yet from the distal end of the barrel 1, and it is necessary to stop the plunger member once and shake the syringe well. When shaking, in order to prevent outflow of the dissolution liquid or the dispersion liquid transferred to the first chamber 4 to the interior of the original second chamber 5, namely to the proximal or rear portion of the cylindrical barrel 1 beyond the sealing member 3c of the plunger member after the reverse flow through the bypass channel 6, this plunger member should be stopped at a suitable position.

After shaking, when the plunger 3c is further advanced, the medicinal liquid is injected through the needle 82. When the rear end of the end sealing member 3c passes the bypass channel 6, the residual liquid within the bypass channel 6 tends to leak backward. Therefore, according to the present invention, the liquid leak preventing element M is arranged at the rear end of the end sealing member 3c.

FIGS. 6 and 7 show an embodiment in which such operations are simplified.

In the example illustrated in FIG. 6, a convex portion 101 projecting circumferentially inward beyond the inner peripheral surface of the cylindrical barrel 1 is formed on the inner peripheral surface of a finger grip 100 mounted to the proximal or rear end portion of the cylindrical barrel 1, and a plurality of lugs 201 are formed in the rod 2 along the same circumference at a predetermined position in the axial direction of the rod. The formation position of each lug 201 in the axial direction of the rod 2 is set to such a position that the lugs 201 are brought into contact with the convex portion 101 of the finger grip 100 such that the leading end face of the forward slidable sealing member 3a reaches ahead of the leading end portion of the bypass channel 6, the rear end face of the backward slidable sealing member 3b is brought into contact with the leading end surface of the end sealing member 3c, and the rear half portion of the end sealing member 3c doesn't enter the bypass channel 6, to maintain a sliding state relative to the inner wall of the cylindrical barrel 1. The distance between the axis of the rod 2 and a point of each lug is a little larger than an inner diameter of the convex portion 101 of the finger grip 100. Further, the material of the finger grip 100 is flexible, for example like a synthetic resin.

Figure 6A:
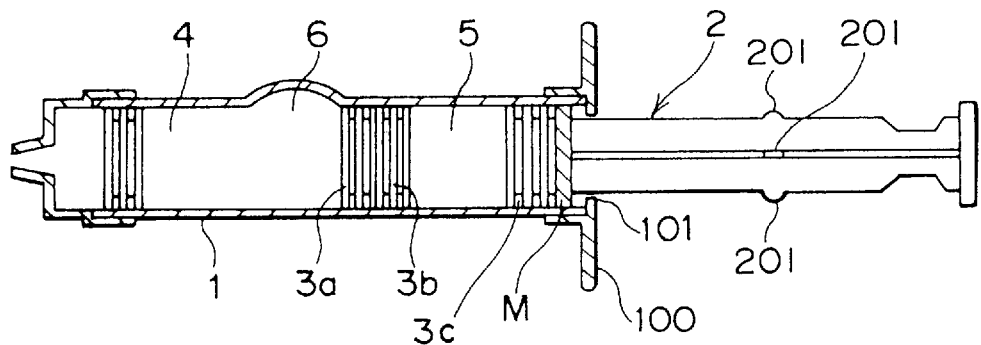
FIGS. 6A to 6C are explanatory views showing steps from the start to the end of an injection mechanism according to the present invention.
Figure 6B:
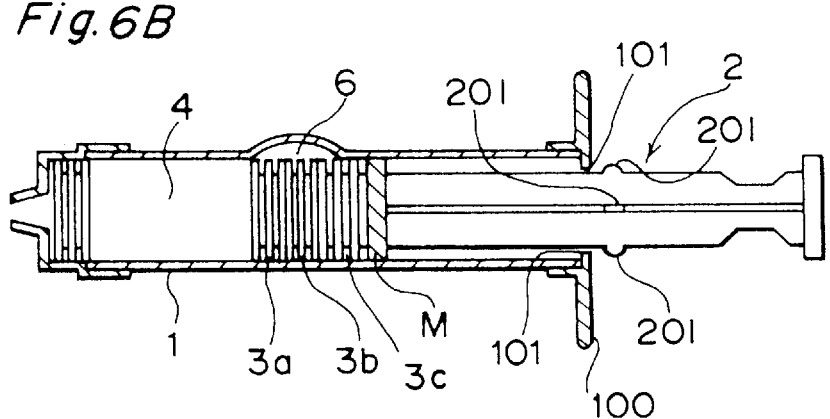
Figure 6C:
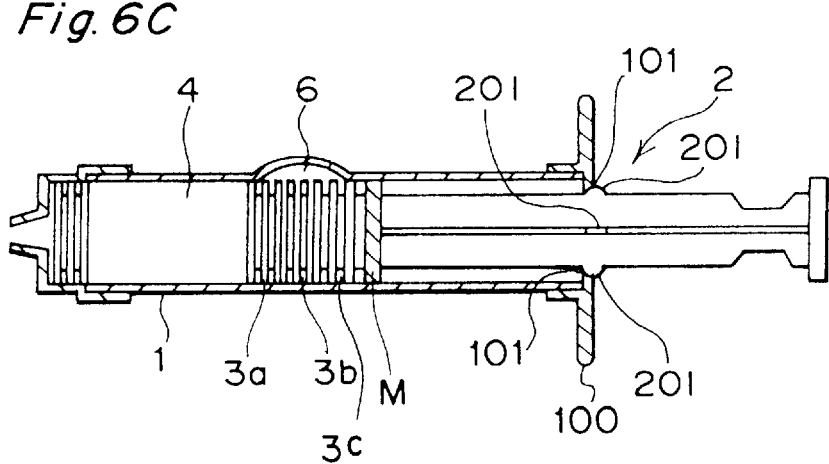

According to the above construction, when the rod 2 is pushed in from an unused condition illustrated in FIG. 6A, the forward slidable sealing member 3a stays near the leading end of the bypass channel 6 during the transfer of the liquid as shown in FIG. 6B. When it is further pushed in, the rod 2 and the end sealing member 3c are stopped once due to a resistance produced by the contact between the lugs 201 and the convex portion 101 as shown in FIG. 6C.

On one hand, in an example shown in FIGS. 7A to 7F, the convex portion 101 is similarly formed on the inner peripheral surface of the finger grip 100 mounted on the rear end portion of the cylindrical barrel 1. As shown in the axial view of FIG. 7B, a plurality of cut-out grooves 102 are formed in this convex portion 101 and the same number of blades 202 are formed in the rod 2. A distance from the center of the rod 2 to the point of each blade 202 is larger than the inner diameter of the convex portion 101 of the finger grip 100 and shorter than a distance from the center of the finger grip 100 to the bottom of each cut-out groove 102. A position of the leading end of each blade 202 is so set that the blades 202 are brought into contact with the rear end face of the finger grip 100 such that the leading end face of the forward slidable sealing member 3a reaches ahead of the leading end portion of the bypass channel 6 owing to the pushing by the end sealing member 3c, the rear end face of the rearward sealing member 3b and the leading end face of the plunger 3c are in contact with each other, and the rear half portion of the end sealing member 3c doesn't enter the bypass channel 6 to maintain a sliding condition relative to the inner wall of the barrel 1.

Figure 7A:
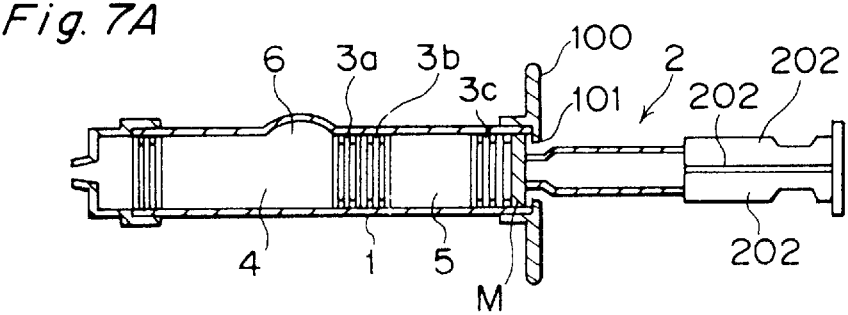
FIGS. 7A to 7F are explanatory views showing steps from the start to the end of injection with a mechanism according to the present invention.
Figure 7B:
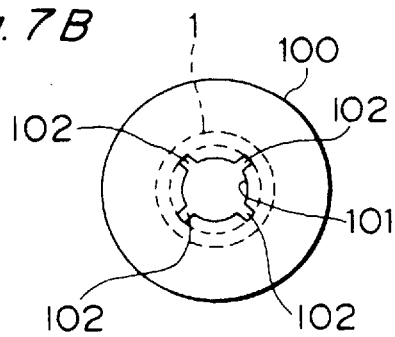
Figure 7C:
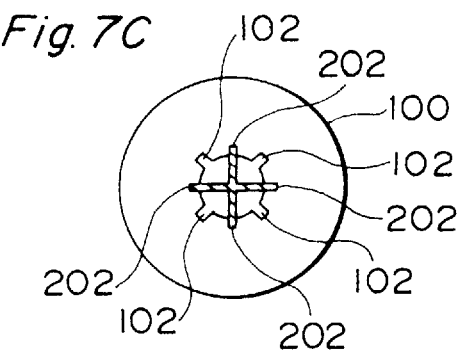
Figure 7D:
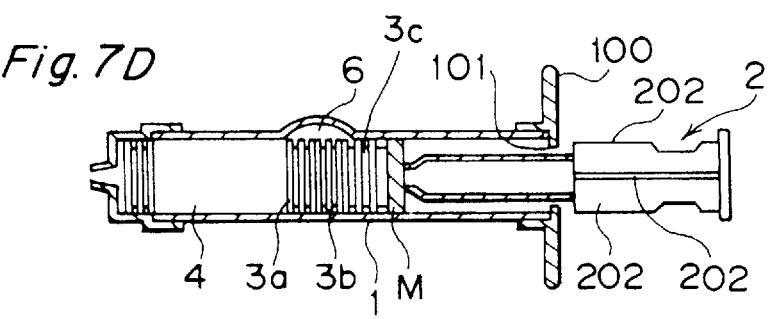
Figure 7E:
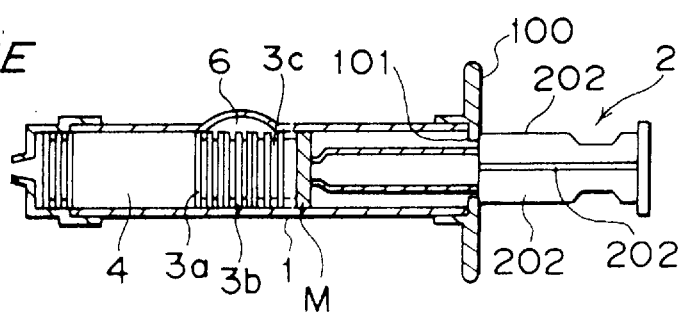
Figure 7F:
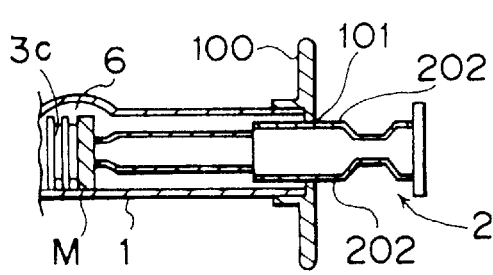

In the above-mentioned construction, in a pre-use condition illustrated in FIG. 7A, the rod 2 is inserted into the cylindrical barrel 1 such that each blade 202 doesn't take the same position as the formation position of the cut-out groove 102 of the finger grip 100 as shown in FIG. 7C. At the time of usage, first the plunger with the rod 2 is pushed in the state of FIG. 7C. Thereby, the forward slidable sealing member 3a stops at the leading end of the bypass channel 6 during the transfer of the liquid, as shown in FIG. 7D. When it is further pushed in, as shown in FIG. 7E, the blades 202 are brought into contact with the rear end face of the finger grip 100 to stop the plunger at that time. Since the liquid within the second chamber 5 has completely flowed into the first chamber 4 as mentioned above, under the condition as well that the reverse flow through the bypass channel 6 is prevented, the two ingredients are uniformly dissolved, dispersed or mixed by shaking the syringe. After that, when each blade 202 is made to take the formation position of each cut-out groove 102 by turning the rod 2, pushing-in of the whole rod becomes possible, as shown in FIG. 7F, and the injection liquid, after the dissolution, the dispersion or the mixing, can be injected into a living body.

By the way, instead of employing the above construction illustrated in FIGS. 6 or FIGS. 7, it is effective merely to provide a line marking in the outer peripheral surface or the inner peripheral surface of the cylindrical barrel 1 along its circumferential direction at a predetermined position in front of the leading end portion of the bypass channel 6, for example at a forward position, by a distance of about 2 mm from the leading end portion of the bypass channel 6. That is, when the plunger is pushed in order that the leading end face of the forward slidable sealing member 3a does not go beyond the marking, the liquid within the second chamber 5 flows nearly completely into the first chamber 4, and then the syringe may be shaken on that condition.

In each already described embodiment, the forward and rearward slidable sealing members 3a, 3b or the end slidable sealing member 3c may be constructed by a plurality of ribs projecting circumferentially from the outer peripheral surfaces thereof, respectively, so as to maintain a liquid-tightness between the first chamber 4 and the second chamber 5 or liquid-tightness between the second chamber 5 and the outside of the barrel 1, in addition to maintaining slidability within the barrel 1. In such a construction, when the respective slidable sealing members 3a, 3b or the slidable sealing member 3c pass over the bypass channel 6 by pushing the rod 2, the liquid remaining within the bypass channel 6 enters an annular concave portion formed between the respective circular ribs of the respective sealing members 3a, 3b or the sealing member 3c of the plunger, resulting in a loss of the injection liquid. In order to resolve this problem, those concave portions may be made shallower to such a degree so as not to worsen the slidability of the sealing member. A countermeasure for further lessening the loss quantity will be described hereinafter.

Figure 8:
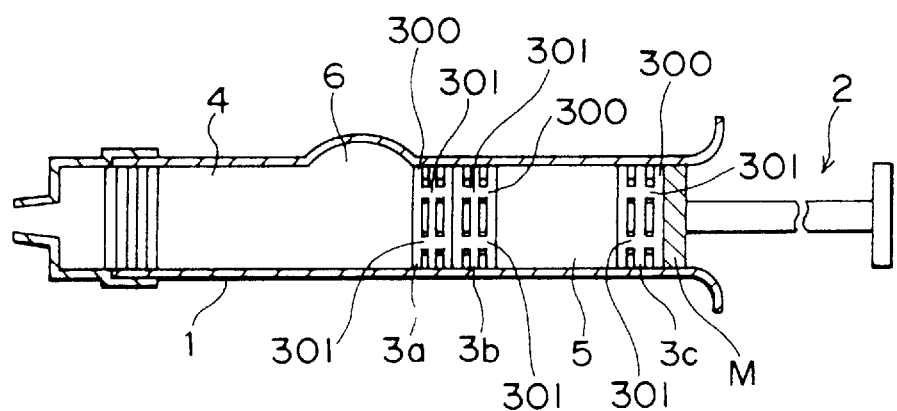
FIG. 8 is a sectional view showing an embodiment to which a countermeasure for decreasing an injecting loss quantity of the injection is applied in a two-ingredient pre-filled syringe of the present invention.

FIG. 8 is a sectional view of an embodiment to which such a countermeasure is applied.

A plurality of circular ribs 300 are formed in the forward slidable sealing member 3a, the rearward slidable sealing member 3b and the end sealing member 3c, respectively, and a plurality of longitudinal ribs 301 are formed between the respective circular ribs so as to have nearly the same height as those of these ribs. Void spaces formed between the respective circular ribs 300 are partitioned by these respective longitudinal ribs 301 into a plurality of smaller void spaces, respectively.

Figure 9:
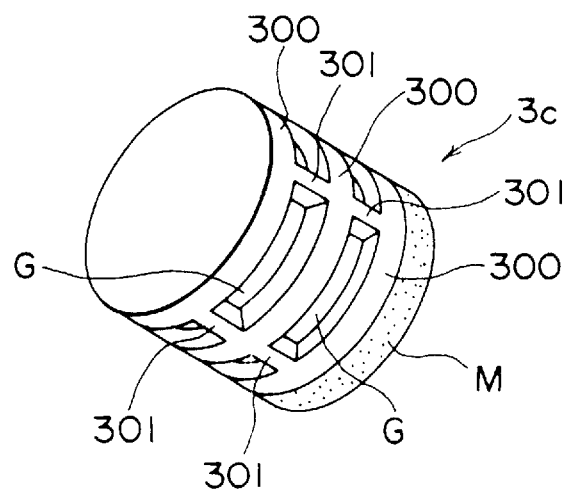
FIG. 9 is a perspective view of respective sealing members 3a, 3b, 3c.
Figure 10:
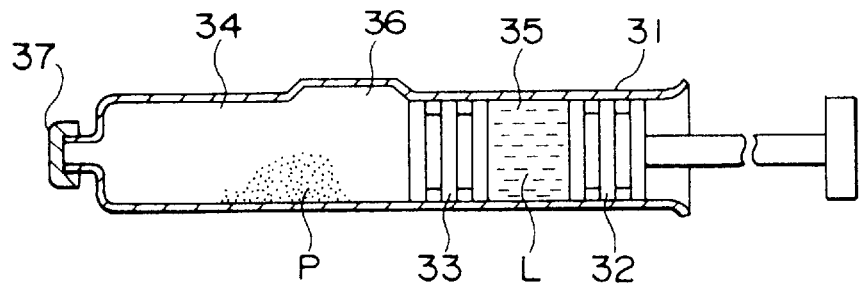
FIG. 10 is a sectional view showing a construction of a conventional two-ingredient pre-filled syringe.
Figure 11:
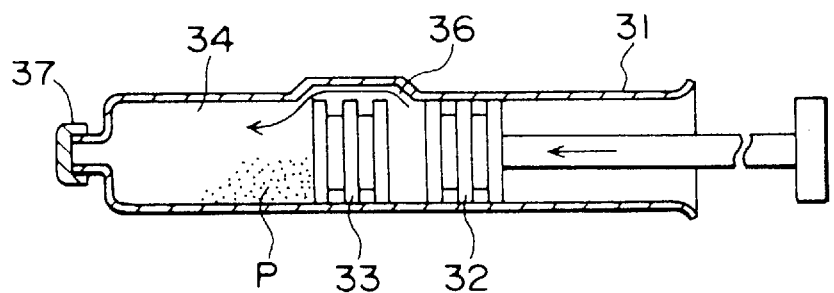
FIG. 11 is an explanatory view of a first operation of the syringe of FIG. 10.
Figure 12:
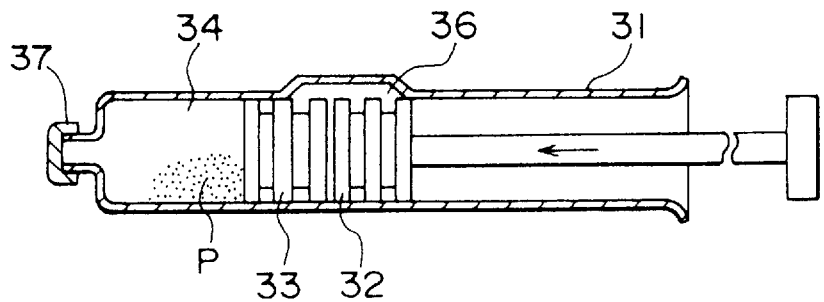
FIG. 12 is an explanatory view of a second operation of the syringe of FIG. 10.

In this embodiment, the four longitudinal ribs 301 are formed within the respective void spaces of the respective sealing members 3a, 3b, 3c at such positions so as to divide the respective outer circumferences equally into four portions, so that the respective void spaces between the circular ribs 300 are divided equally into four portions (refer to FIG. 9).

Such a construction, when the forward slidable sealing member 3a, the rearward slidable sealing member 3b and the end slidable sealing member 3c pass over the bypass channel 6 owing to the pushing of the rod 2, makes the injection liquid enter any one of the small void spaces partitioned by the longitudinal ribs 301 of the void spaces between the respective circular ribs 300 through this bypass channel 6. But, the injection liquid can not enter the adjacent small void spaces because of the existence of the longitudinal ribs 301, so that the residual injection liquid within the void spaces of the respective sealing members decreases to about ¼ in comparison with the case in which only the circular ribs 300 are provided.

The number of the longitudinal ribs 301 arranged within the respective void spaces between the circular ribs 300 is not limited to four, but can be optionally selected to be at least two. While it becomes possible to decrease the loss quantity of the injection liquid as the number thereof increases, since the slidability of each sealing member lowers accordingly, it is preferable to select a suitable number in consideration of both. The longitudinal ribs 301 may be formed only in the forward and the rearward slidable sealing members 3a, 3b.

In the respective circular ribs 300 and longitudinal ribs 301 of the forward and the rearward slidable sealing members 3a, 3b and the sealing member 3c of the plunger, their axial configurations may be formed with a crowning, having a swell which is suitably curved axially to decrease frictional resistance relative to the cylindrical barrel 1, instead of linearly along the inner wall surface of the cylindrical barrel 1 as illustrated.

The above-mentioned liquid-absorbent element M may be formed from the cylindrical liquid-absorbent member R slidable relative to the cylindrical barrel and detachably mounted to the leading end portion of the plunger rod. This liquid-absorbent material R is manufactured by stamping a liquid-absorbent material sheet in a predetermined configuration, which may be selected from the group consisting of polyvinylformal, polyester fiber, pulp, polyester fiber containing pulp, polyester fiber containing acetate fiber, acetate fiber, cellulose sponge, polyvinyl alcohol sponge and liquid-absorbent resin and may be impregnated by dipping with a water-holding and liquid-absorbing accelerator, which may be selected from the group consisting of glycerine, propylene glycol, polyethylene glycol, D-sorbitol, polyoxyethylene cetyl ether, and benzyl alcohol. It may be made cylindrical by stacking the above-mentioned disk-shaped liquid-absorbent materials D as shown in FIG. 15. The liquid-absorbent material may be impregnated with an antimicrobial active agent selected from benzalkonium chloride, benzethonium chloride, dodecyldiaminoethylglycine, dodecyldimethylbenzylammonium chloride, polyhexa-methylenebiguanide and alkyldiaminoethylglycine hydrochloride.

In this case, as shown in FIG. 23, since the cylindrical liquid-absorbent material R is longer in its total length in the advancing direction (usually at least 10 mm in the total length) in comparison with the disk-shaped liquid-absorbent material D as shown in FIG. 15, sufficient liquid-absorbing and holding can be attained even when dropping timing of the residual liquid gets delayed a little when the cylinder is passed over the bypass channel. Further, when the end portion slidable sealing member is completely pushed, the cylindrical liquid-absorbent material R is usually pushed forward beyond the bypass channel. But, especially as shown in FIG. 24, when its rear end can stay there so as to pass over the bypass channel, the function of preventing leaking of the residual liquid is great. In the above embodiment, the same component members as those in FIG. 6 are designated by the same numbers, and the explanations thereof are omitted.

Although the present invention has been fully described by way of examples with reference to the accompanying drawings, it is to be noted here that various changes and modifications will be apparent to those skilled in the art.

Therefore, unless such changes and modifications otherwise depart from the spirit and scope of the present invention, they should be construed as being included therein.

What is claimed is:

1. A syringe comprising:
    a tubular barrel having distal and proximal ends opposite to each other and also having an interior hollow defined therebetween, said distal end portion being sealed and engageable with a needle for injection of medical substances to be mixed in said interior and said proximal end portion being sealed by an end slidable sealing member connectable with a rod for making said end slidable sealing member slidable in an axial direction in said barrel;
    at least one intermediate sealing member inserted into said barrel, said intermediate sealing member dividing an interior of said barrel in a sealed manner into a first chamber for recieving a first medical substance and a second chamber for receiving a second medical substance, said intermediate sealing member being slidable in said barrel in response to sliding of said end slidable sealing member in said barrel;
    at least one bypass portion formed axially along said barrel between said intermediate slidable sealing member and said distal end portion, said bypass portion permitting said second medical substance to bypass said intermediate slidable sealing member and be introduced into said first medical substance to be mixed therewith;
    wherein said intermediate slidable sealing member has an axial length or thickness shorter than that of said bypass portion;
    at least one liquid-absorbent element capable of absorbing the liquid and holding it therein, said liquid-absorbent element positioned behind one of end face of said end sealing member opposite to said second chamber in said barrel.

2. A syringe as set forth in claim 1, wherein said liquid-absorbent element is positioned just behind said one end face of said end sealing member opposite to said second chamber in said barrel.

3. A syringe as set forth in claim 1, wherein said liquid-absorbent element is positioned at some interval behind said one end face of said end sealing member opposite to said second chamber in said barrel.

4. A syringe as set forth in claim 1, wherein said end sealing member is provided integrally with one end of the rod and said liquid-absorbent element is connected detachably with one of the end faces of said end sealing member opposite to said second chamber.

5. A syringe as set forth in claim 1, wherein said end sealing member is provided integrally with said one end of the rod and liquid-absorbent element is connected integrally with one of the end faces of said end sealing member opposite to said second chamber.

6. A syringe as set forth in claim 1, wherein said end sealing member is provided detachably with one end of the rod and said liquid-absorbent element is connected detachably with one of the end faces of said end sealing member opposite to said second chamber.

7. A syringe as set forth in claim 1, wherein said end sealing member is provided detachably with one end of the rod and said liquid-absorbent element is connected integrally with one of the end faces of said end sealing member opposite to said second chamber.

8. A syringe as set forth in claim 1, wherein the liquid-absorbent element is made of a liquid-absorbent material selected from the group consisting of papers, fibers and resins having a liquid-absorbent capability.

9. A syringe as set forth in claim 8, wherein said liquid-absorbent material is at least one selected from the group of polyvinylformal, polyester fibers, pulps, polyester fibers containing pulps and acetate fibers, acetate fibers, sponges and absorbing resins.

10. A syringe as set forth in claim 8, wherein said liquid-absorbent material contains a water-holding and liquid-absorbing accelerator for accelerating its liquid-absorbing effect.

11. A syringe as set forth in claim 10, wherein said water-holding and liquid-absorbing accelerator comprises at least one kind of material selected from the group consisting of glycerine, propylene glycol, polyethylene glycol, D-sorbitol, polyoxyethylene cetyl ether, and benzyl alcohol.

12. A syringe as set forth in claim 8, wherein said liquid-absorbent material contains a water-holding and liquid-absorbing accelerator and an interfacial active agent.

13. A syringe as set forth in claim 8, wherein said liquid-aborbent material contains an antimicrobial active agent.

14. A syringe as set forth in claim 8, wherein said liquid-absorbent material contains a water-holding and liquid-absorbing accelerator and an antimicrobial active agent.

15. A syringe as set forth in claim 13, wherein said antimicrobial active agent comprises at least one kind of material selected from the group consisting of benzalkonium chloride, benzethonium chloride, dodecyldiaminoethylglycine, dodecyldimethylbenzylammonium chloride, polyhexamethylenebiguanide, cetylpyridium chloride and akyl-diaminoethylglycine hydrochloride.

16. A syringe as set forth in claim 8, wherein said liquid-absorbent material contains a coloring agent.

17. A syringe as set forth in claim 8, wherein said liquid-absorbent material contains a deactivating agent.

18. A syringe as set forth in claim 8, wherein said liquid-absorbent material contains a deactivating and a coloring agent.

19. A syringe as set forth in claim 1, wherein said liquid-absorbent element substantially has no clearance between its outer circumference and an inner wall of the syringe.

20. A syringe as set forth in claim 1, wherein said liquid-absorbent element has a clearance between its outer circumference and a inner wall of the syringe and contains an water-holding and liquid-absorbing accelerator.

21. A syringe as set forth in claim 1, wherein said liquid-absorbent element has a cylindrical shape having a central through hole adapted to be fitted into one end of the rod, said rod being detachable from the end slidable sealing member.

22. A syringe as set forth in claim 21, wherein said cylindrical shaped absorbing element is made of a polyvinylformal sponge sheet containing glycerine as a liquid-absorbent acceralator and benzalkonium chloride as an antimicrobial active agent.

23. A syringe as set forth in claim 1, wherein said liquid-absorbent element comprises an annular or spiral groove capable of absorbing liquid.

24. A syringe as set forth in claim 1, wherein said liquid-absorbent element is a liquid-absorbent material wound like a ring on at least a leading end portion of the rod.

25. A syringe as set forth in claim 1, wherein said liquid-absorbent element is an end stopper for closing a proximal one of end openings of said barrel and having a central through hole for slidably inserting the rod therein.

26. A syringe as set forth in claim 1, wherein said liquid-absorbent element is an end stopper fitted into a finger grip mounted onto a proximal one of opposite ends of said barrel.

27. A syringe as set forth in claim 1, wherein said liquid-absorbent element comprises a sealing material arranged in a sliding manner with said end sealing member and an end stopper having a central through hole for inserted slidably the rod therein and positioned at a proximal one of end openings of said barrel in a non-sidable manner.

28. A syringe as set forth in claim 14, wherein said antimicrobial active agent comprises at least one kind of material selected from the group consisting of benzalkonium chloride, benzethonium chloride, dodecyldiaminoethylglycine, dodecyldimethylbenzylammonium chloride, polyhexamithylenebiguanide, cetylpyridium chloride and alkyl-diaminoethylglycine hydrochloride.

* * * * *